(12) United States Patent
Kitaoka et al.

(10) Patent No.: US 11,559,321 B2
(45) Date of Patent: Jan. 24, 2023

(54) MEDICAL DEVICE

(71) Applicant: TERUMO KABUSHIKI KAISHA, Tokyo (JP)

(72) Inventors: Takashi Kitaoka, Hadano (JP); Mizuho Shiraishi, Sagamihara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 99 days.

(21) Appl. No.: 17/023,518

(22) Filed: Sep. 17, 2020

(65) Prior Publication Data
US 2021/0000494 A1    Jan. 7, 2021

Related U.S. Application Data

(63) Continuation of application No. PCT/JP2019/011688, filed on Mar. 20, 2019.

(30) Foreign Application Priority Data

Mar. 29, 2018    (JP) .............................. JP2018-064010

(51) Int. Cl.
   *A61B 17/221* (2006.01)
   *A61B 17/00* (2006.01)
   *A61B 17/22* (2006.01)

(52) U.S. Cl.
   CPC .. *A61B 17/221* (2013.01); *A61B 2017/00477* (2013.01); *A61B 2017/2212* (2013.01);
   (Continued)

(58) Field of Classification Search
   CPC .......... A61B 17/221; A61B 17/320725; A61B 17/320758; A61B 2017/00477;
   (Continued)

(56) References Cited

U.S. PATENT DOCUMENTS 5,490,859 A    2/1996  Mische et al.
5,836,868 A *  11/1998 Ressemann .... A61B 17/320725
                                                606/159
(Continued)

FOREIGN PATENT DOCUMENTS

JP    H08509639 A      10/1996
JP    2003504090 A      2/2003
JP    2017221665 A     12/2017

OTHER PUBLICATIONS

The extended European Search Report dated May 17, 2021, by the European Patent Office in corresponding European Patent Application No. 19776732.0-1113. (8 pages).
(Continued)

*Primary Examiner* — Mohamed G Gabr
(74) *Attorney, Agent, or Firm* — Buchanan Ingersoll & Rooney PC

(57) ABSTRACT

A medical device capable of adjusting, while a rotating expandable portion breaks an object, a breaking force of the expandable portion. The medical device for breaking a thrombus in a blood vessel includes a shaft portion, an expandable portion that is provided to the shaft portion, a fixing portion that fixes the expandable portion and the shaft portion, a slide portion that is fixed to the expandable portion and is slidable with the shaft portion, and an outer tube that houses therein the shaft portion, in which the slide portion is movable by being indirectly pressed by the outer tube, and the slide portion is relatively rotatable relative to the outer tube.

19 Claims, 5 Drawing Sheets

(52) U.S. Cl.
CPC .............. *A61B 2017/22051* (2013.01); *A61B 2017/22078* (2013.01)

(58) Field of Classification Search
CPC ........... A61B 2017/22051; A61B 2017/22078; A61B 2017/2212; A61B 2017/320733; A61B 2090/034; A61B 2090/08021
See application file for complete search history.

(56) References Cited

U.S. PATENT DOCUMENTS

| | | |
|---|---|---|
| 2006/0229645 A1 | 10/2006 | Bonnette et al. |
| 2016/0354108 A1 | 12/2016 | Nakano et al. |
| 2017/0354435 A1 | 12/2017 | Hatta et al. |

OTHER PUBLICATIONS

International Search Report (PCT/ISA/210) dated Jun. 4, 2019, by the Japanese Patent Office as the International Searching Authority for International Application No. PCT/JP2019/011688.

An English Translation of the International Search Report (Form PCT/ISA/210) and the Written Opinion of the International Searching Authority (Form PCT/ISA/237) dated Jun. 4, 2019, by the Japanese Patent Office in corresponding International Application No. PCT/JP2019/011688. (8 pages).

\* cited by examiner

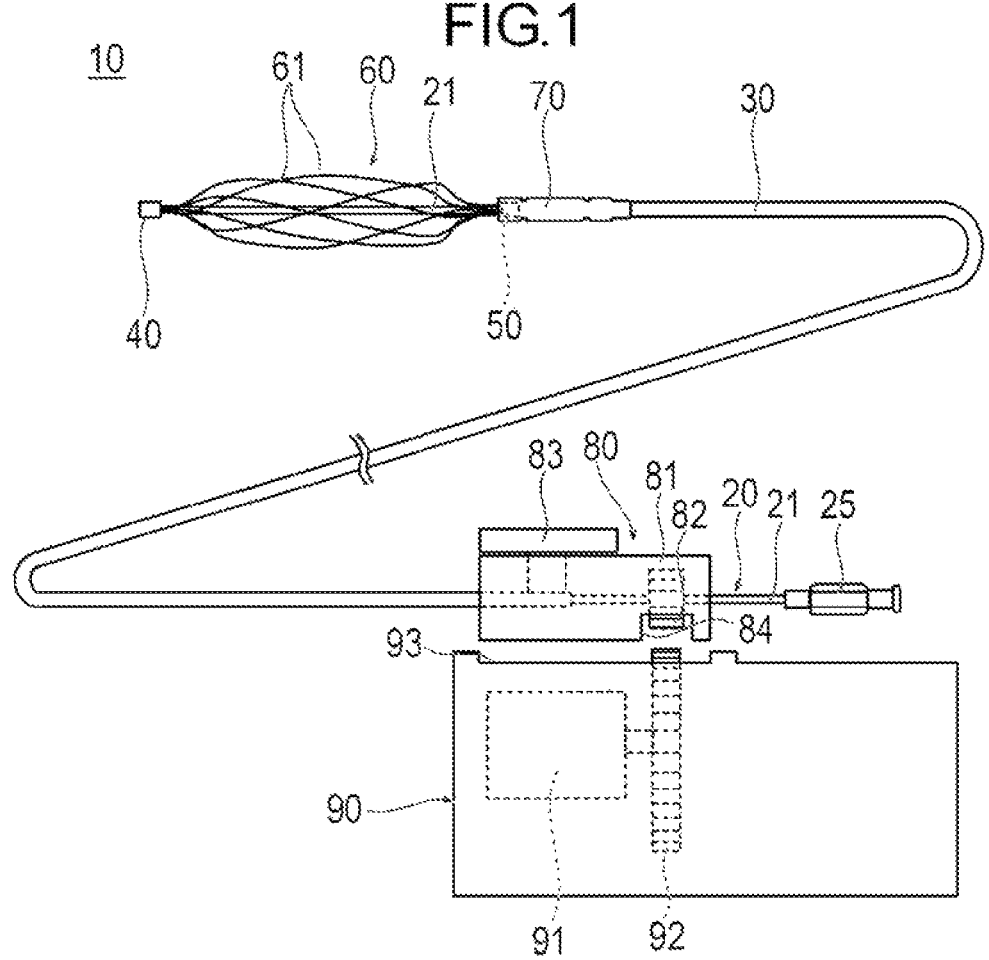
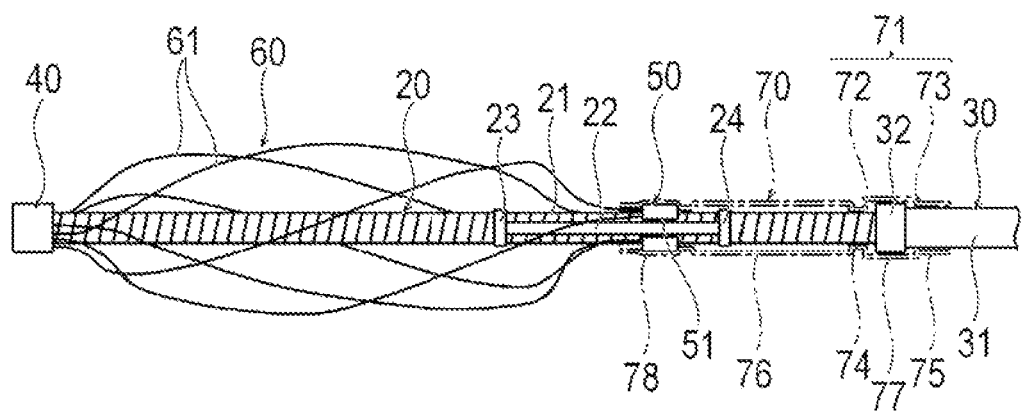

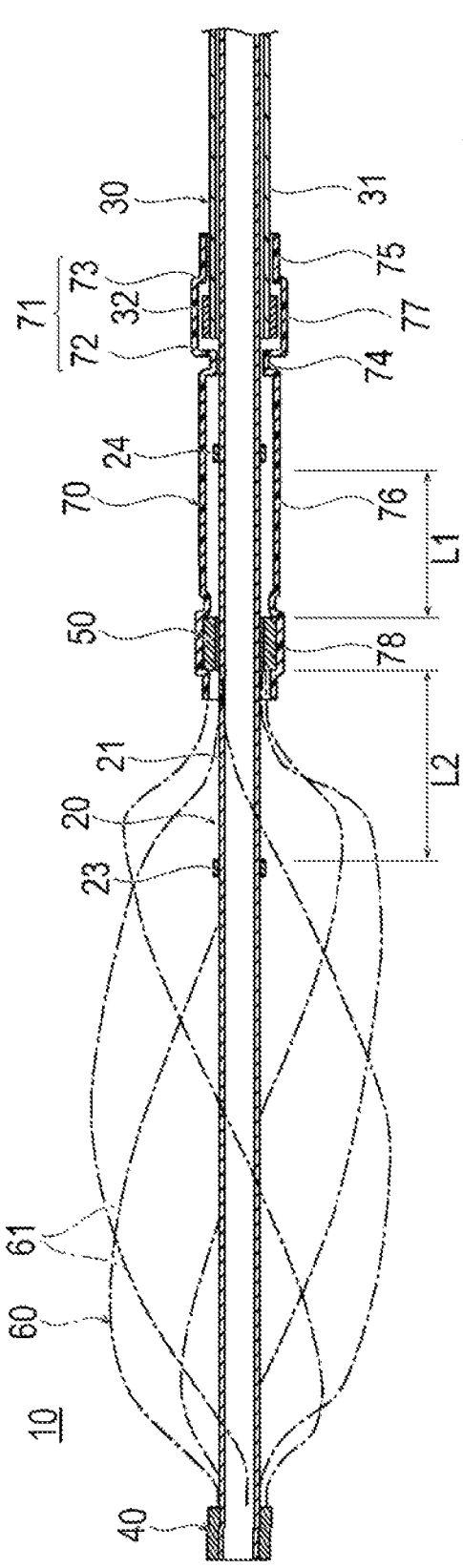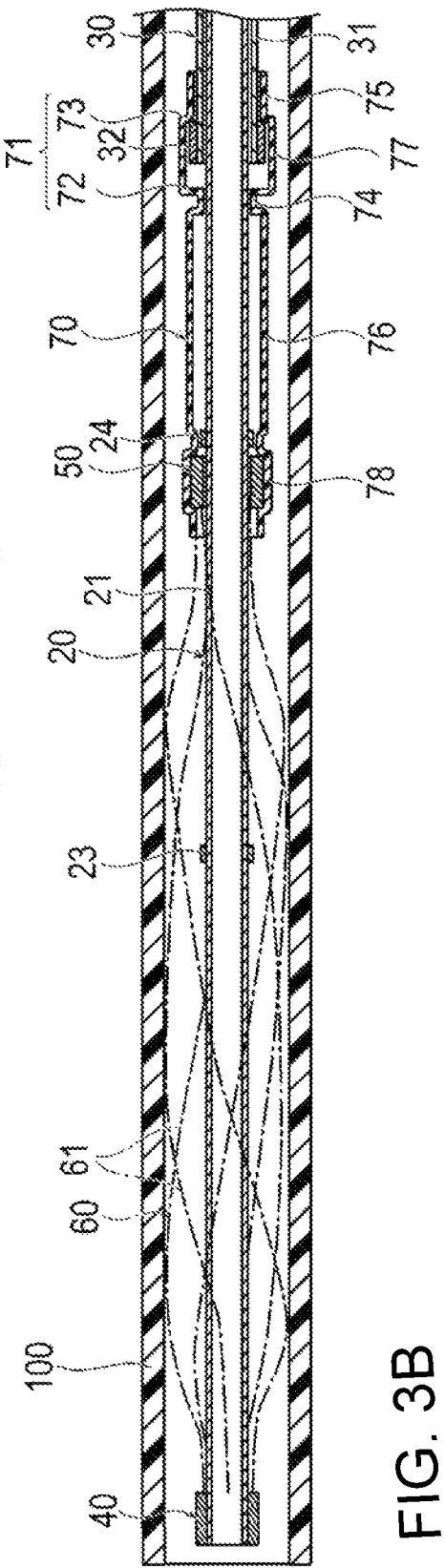
FIG. 3A
FIG. 3B

MEDICAL DEVICE

CROSS-REFERENCES TO RELATED APPLICATIONS

This application is a continuation of International Application No. PCT/JP2019/011688 filed on Mar. 20, 2019, which claims priority to Japanese Patent Application No. 2018-064010 filed on Mar. 29, 2018, the entire content of both of which is incorporated herein by reference.

FIELD OF THE INVENTION

This disclosure generally relates to a medical device for removing an object in a body lumen.

BACKGROUND DISCUSSION

A thrombus generated in a body lumen needs to be promptly removed. A known method for treating a thrombus involves breaking and removing the thrombus by an inflation portion provided at a distal side of an elongated shaft portion. The inflation portion changes an inflated diameter thereof depending on a change in length in an axial direction.

For example, JP-T 2003-504090 describes a device that cuts a thrombus in a coronary artery. This device is provided with a rotating body at a distal portion of a catheter, wherein an abradant is adhered to the outer surface of the rotating body. This device rotates the rotating body in the coronary artery, thereby cutting a stenosis substance by the abradant. The rotating body of this device is provided with four bars that are arranged in a circumferential direction. The rotating body is capable of inflating in accordance with a diameter of a blood vessel by bending and protruding the bars radially outward.

SUMMARY

When an object to be broken is difficult to break, there may be a desire to increase the breaking force. However, the abovementioned device described in JP-T 2003-504090 cannot change the inflated diameter of the bar when the rotating body is rotating.

The medical device disclosed here allows adjustment of a breaking force of an expandable portion when the rotating expandable portion breaks an object.

A medical device disclosed here is able to destroy (e.g., crush or cut) an object in a body lumen. The medical device includes an axially movable outer tube possessing an interior, an elongated shaft that is configured to be rotationally driven, and an expandable portion positioned at a distal portion of the elongated shaft. At least a part of the elongated shaft is positioned in the interior of the outer tube, and the outer tube and the elongated shaft are relatively axially movable. The expandable portion is outwardly expandable from a contracted state to an expanded state. A fixing portion fixes the distal end of the expandable portion to the distal end of the shaft portion so that axial movement of the elongated shaft in the axial direction results in axial movement of the expandable portion in the axial direction and so that rotation of the elongated shaft results in rotation of the expandable portion. A slide portion is slidably mounted on the elongated shaft to slide in the axial direction along the elongated shaft, wherein the slide portion is fixed to the proximal end of the expandable portion so that sliding movement of the slide portion along the elongated shaft results in sliding movement of the proximal end of the expandable portion along the elongated shaft. The slide portion is movable by being directly or indirectly pressed by the outer tube, and the slide portion and the outer tube are relatively rotatable with respect to one another.

In the medical device configured as the above, the slide portion can be caused to move to the distal side or the proximal side by causing the outer tube to move in the axial direction. The slide portion moves to the distal side or the proximal side to deform the inflation portion that is positioned between the fixing portion and the slide portion. In addition, the interlock portion relatively rotates relative to the outer tube. Therefore, in the medical device, during when the rotating inflation portion is breaking the object, it is possible to adjust the breaking force of the inflation portion and to prevent the rotation force from the rotating slide portion from being transmitted to the outer tube, which results in an easy operation by an operator.

According to another aspect, a medical device for destroying an object in a body lumen comprises: an axially movable outer tube possessing an interior; an elongated shaft that is configured to be rotationally driven; and an expandable portion. At least a part of the elongated shaft is positioned in the interior of the outer tube, and the outer tube and the elongated shaft are relatively axially movable in an axial direction. The expandable portion is comprised of a plurality of wires each having shape memory characteristics. The plurality of wires at least in the intermediate part of the expandable portion being spaced apart from one another, and the expandable portion being outwardly expandable from a contracted state to an expanded state by virtue of a self-elastic force of each of the plurality of wires, with the expandable portion moving a first distance in the axial direction as the expandable portion moves from the contracted state to the expanded state, and the expandable portion in the expanded state possessing a first outer diameter. A fixing portion fixes the distal end of each of the plurality of wires to the distal end of the elongated shaft, and a slide portion is slidably mounted on the elongated shaft to slide in the axial direction along the elongated shaft. The slide portion is axially slidable in the axial direction relative to the elongated shaft, and is fixed to the proximal end of each of the plurality of wires so that sliding movement of the slide portion along the elongated shaft results in sliding movement of the proximal end of each of the plurality of wires along the elongated shaft. A distal side stopper and a proximal side stopper are fixed to the elongated shaft to restrict movement of the slide portion, and the axial distance between the distal side stopper and the proximal side stopper is greater than the first distance. The expandable portion expands outwardly from the first outer diameter to a second outer diameter that is larger than the first outer diameter when the outer tube is moved in the axial direction by a second distance so that the slide portion moves toward the distal side stopper.

In accordance with another aspect, a method comprises positioning an expandable portion in a living body lumen in a living body while the expandable portion is in a contracted state, wherein the expandable portion is positioned at a distal portion of an elongated shaft; moving the expandable portion in the living body lumen to position the expandable portion adjacent an object in the living body lumen that is to be cut; expanding the expandable portion from the contracted state to a first expanded state to increase an outer size of the expandable portion; rotating the expandable portion while the expandable portion is in the first expanded state to cause the rotating expandable portion in the first expanded state to cut the object; and further expanding the expandable portion from the first expanded state to a second expanded state in which the outer size of the expandable portion in the second expanded state is greater than the outer size of the expandable portion in the first expanded state. The further expanding of the expandable portion from the first expanded state to the second expanded state occurs while the expandable portion is rotating. The method additionally involves rotating the expandable portion while the expandable portion is in the second expanded state to cause the rotating expandable portion in the second expanded state to further cut the object.

BRIEF DESCRIPTION OF THE DRAWINGS

FIG. 1 is a plan view illustrating a medical device according to an embodiment.

FIG. 2 is an enlarged plan view illustrating a distal portion of the medical device.

FIGS. 3(A) and 3(B) depict cross-sectional views illustrating the distal portion of the medical device: FIG. 3(A) illustrates a state where an expandable portion has expanded; and FIG. 3(B) illustrates a state where the expandable portion has contracted.

DETAILED DESCRIPTION

Figure 4:
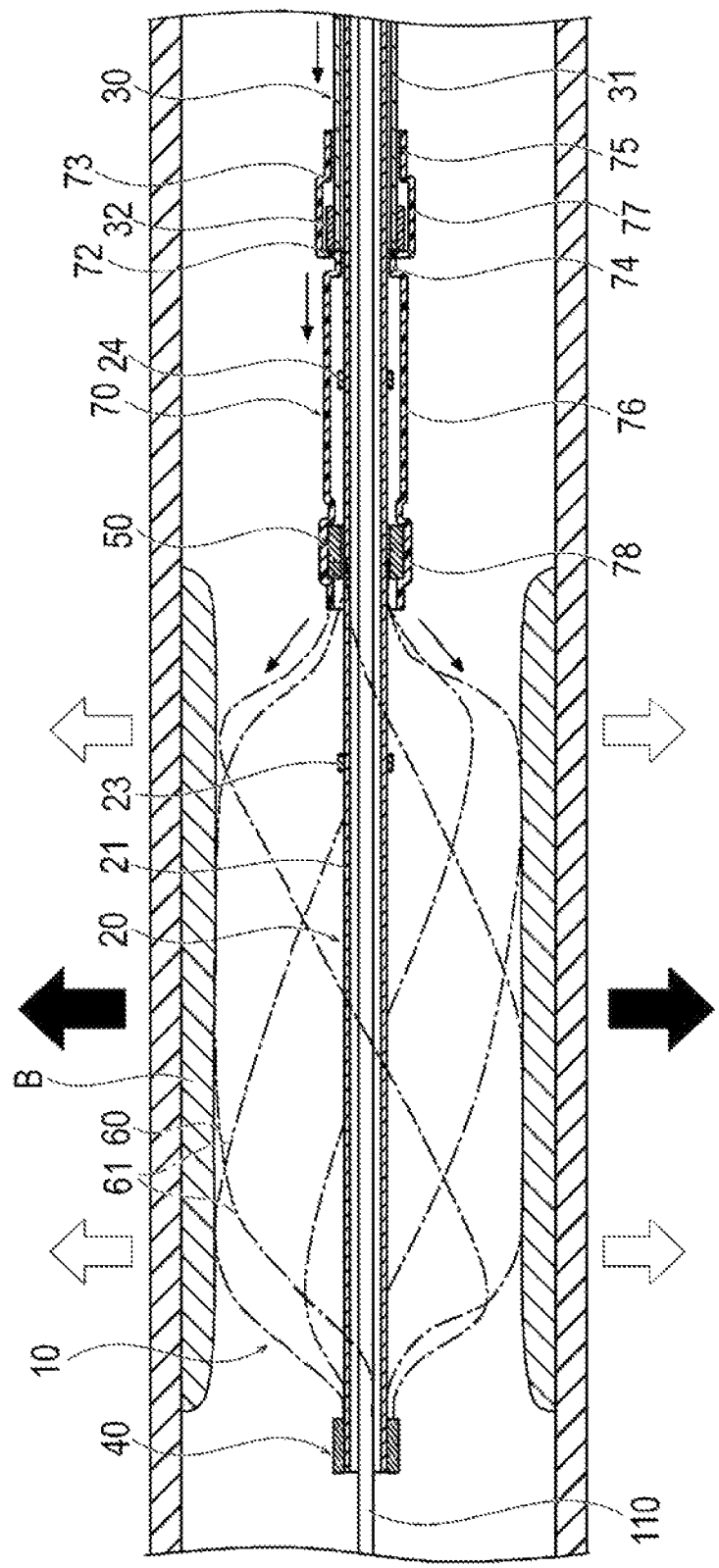
FIG. 4 is a cross-sectional view illustrating a state where the expandable portion is caused to further outwardly expand in a blood vessel.

Set forth below with reference to the accompanying drawings is a detailed description of embodiments of a medical device and method of use representing examples of the inventive medical device and method disclosed here. The dimensions or scales on the drawings may be exaggerated or different from actuality/reality for convenience of description and illustration.

A medical device 10 according to one embodiment disclosed by way of example is inserted into a blood vessel in a deep venous thrombosis, and is used for a procedure to break the thrombus. In the present description, a side of a device to be inserted into the blood vessel is referred to a "distal side" or "distal end", and a hand-side where the device is operated is referred to as a "proximal side" or "proximal end". An object to be broken through use of the medical device and method disclosed here is not necessarily limited to a thrombus, and all objects that can exist in a body lumen can be corresponded.

The medical device 10 includes, as illustrated in FIGS. 1, 2, and 3(A), a shaft portion 20, an outer tube 30, an expandable portion 60, a fixing portion 40, a slide portion 50, an interlock portion 70, an operation unit 80, and a driving unit 90.

The shaft portion (shaft) 20 is a portion that transmits a rotation force to the expandable portion 60. The shaft portion 20 is provided with a shaft body (shaft) 21, a guide convex portion 22, a distal side stopper 23, a proximal side stopper 24, and a hub 25. The shaft body 21 is an elongated tubular body that transmits the rotation force from a proximal portion of the shaft body 21 to a distal portion of the shaft body 21. The proximal portion of the shaft body 21 penetrates through the operation unit 80. The proximal portion of the shaft body 21 is rotatably connected to the operation unit 80. The shaft body 21 has flexibility so as to be able to move in the blood vessel. In addition, the shaft body 21 has preferably high torsional rigidity so as to be able to transmit the rotation force from the proximal portion of the shaft body 21 to the distal portion of the shaft body 26. The shaft portion 20 is, for example, a tubular body made of metal in which a spiral-shaped slit is formed. Examples of a material from which the shaft portion 20 may be made include stainless steel.

The hub 25 is fixed to a proximal end of the shaft body 21. The hub 25 allows a guide wire to be inserted therethrough.

The guide convex portion 22 is fixed to an outer peripheral surface of the shaft body 21 at a distal portion of the shaft body 21 so that the guide convex portion 22 moves together with the shaft body 21. The guide convex portion 22 is elongated, and is disposed parallel to an axial center or center axis of the shaft body 21. The guide convex portion 22 restricts or prevents the rotation of the slide portion 50, and transmits the rotation force to the slide portion 50. Moreover, the guide convex portion 22 causes the slide portion 50 to move along the central axis of the shaft body 21.

The distal side stopper 23 is a ring-shaped member that is fixed to the outer peripheral surface of the shaft body 21 on the distal side of the guide convex portion 22. The distal side stopper 23 restricts movement of the slide portion 50 to the distal side or in the distal direction. The proximal side stopper 24 is a ring-shaped member that is fixed to the outer peripheral surface of the shaft body 21 on the proximal side of the guide convex portion 22. The proximal side stopper 24 restricts the movement of the slide portion 50 to the proximal side or in the proximal direction.

The fixing portion 40 is a tubular member that fixes the expandable portion 60 to the shaft portion 20. The fixing portion 40 is fixed to the outer peripheral surface of the shaft body 21 at a distal end of the shaft body 21. In addition, the fixing portion 40 is fixed to a distal end of the expandable portion 60.

The slide portion or slide piece 50 is a member that is slidably positioned on the outer peripheral surface of the shaft body 21 on the proximal side from the fixing portion 40. A proximal end of the expandable portion 60 is fixed to the slide portion 50. The slide portion 50 has an approximately C-character shape in a cross-section orthogonal to the central axis of the shaft body 21. In other words, an axially extending slit-shaped guide groove 51 is formed in the slide portion 50 from a distal end of the slide portion 50 to a proximal end of the slide portion 50. The guide convex portion 22 is disposed in the guide groove 51. Accordingly, the slide portion 50 is capable of sliding on and relative to the outer peripheral surface of the shaft body 21 in the axial direction along the guide convex portion 22. Moreover, the rotation of the slide portion 50 is restricted or prevented by the guide convex portion 22. Accordingly, when the shaft portion 20 rotates, the slide portion 50 receives the rotation force from the guide convex portion 22. Therefore, the slide portion 50 is movable in the axial direction relative to and along the shaft portion 20, and can rotate together with the shaft portion 20.

The expandable portion 60 is a portion that outwardly expands in the body lumen, and rotates to break an object such as a thrombus. The expandable portion 60 is provided at the distal portion of the shaft portion 20. The expandable portion 60 includes a plurality of (six in the present embodiment) wire rods 61. Each of the wire rods 61 is three-dimensionally curved. The number of the wire rods 61 is not specially limited. Moreover, the cross-sectional shape of wire rod 61 is not specially limited. A twist toward the same circumferential direction is applied to each of the wire rods 61 along the axial direction of the shaft portion 20, meaning each of the wire rods extends in a helical manner as shown in FIG. 2. As illustrated, the wires or wire rods 61 are separate from one another and spaced apart from one another at least in the axially intermediate portion of the expandable portion 60. Distal ends of the respective wire rods 61 are fixed to the fixing portion 40. Proximal ends of the respective wire rods 61 are fixed to the slide portion 50. Fixed positions of the respective wire rods 61 relative to the fixing portion 40 and the slide portion 50 are aligned in the circumferential direction. Moreover, curved approximately center parts of the respective wire rods 61 are aligned in the circumferential direction at positions distant from the shaft portion 20 in the radial direction. Accordingly, the expandable portion 60 has a uniform swelling in the circumferential direction as a whole. The expandable portion 60 becomes a first expanded state in a natural state where no external force acts. When the shaft portion 20 rotates, the expandable portion 60 also rotates with the rotation, and can break a thrombus in the blood vessel and stir the broken thrombi.

The wire rods 61 included in the expandable portion 60 are each a relatively thin member made of metal and having flexibility. The expandable portion 60 is in a state of being housed in an inside of a sheath 100 before reaching a target site in the blood vessel, as illustrated in FIG. 3(B). The sheath 100 may be of a known construction. When the expandable portion 60 is inserted into or positioned in the sheath 100, the slide portion 50 moves along the shaft portion 20 to the proximal side, and is separated from the fixing portion 40. Accordingly, the wire rods 61 are reduced in diameter and housed in an inside of the sheath 100. After the shaft portion 20 is inserted to or positioned at the target site in the blood vessel, the sheath 100 is caused to move to the proximal side relative to the shaft portion 20. Accordingly, as illustrated in FIGS. 2 and 3(A), the expandable portion 60 is exposed to an outside of the sheath 100 at a position distal of the distal end of the sheath 100, and automatically expands by a self-elastic or self-expanding force of the expandable portion 60. At this time, the slide portion 50 moves along the shaft portion 20 to the distal side or in the distal direction.

The wire rods 61 desirably include a material having shape memory characteristics so as to be highly elastically deformed. Examples of a material from which the wire rods 61 may be made include a shape memory alloy to which a shape memory effect and super elasticity are applied by thermal processing, stainless steel, and the like. As for a shape memory alloy, Ni—Ti-based, Cu—Al—Ni-based, Cu—Zn—Al-based alloys, combinations thereof, and the like are suitable.

The outer tube 30 is a member that transmits a movement force toward the axial direction at a hand-side (proximal end) to the distal side. The outer tube 30 includes an outer tube main body 31 and a press-side engagement portion 32. The outer tube main body 31 is a tubular body that rotatably houses therein the rotating shaft body 21. The outer tube main body 31 has flexibility so as to be able to move in the blood vessel. The outer tube main body 31 is movable in the axial direction along the shaft body 21. A proximal portion of the outer tube main body 31 is positioned in an inside of the operation unit 80. The press-side engagement portion 32 is a ring-shaped member that is fixed to an outer peripheral surface of the outer tube main body 31 at a distal end of the outer tube main body 31. The press-side engagement portion 32 protrudes from the outer peripheral surface of the outer tube main body 31 outward in the radial direction. A surface on the distal side of and a surface on the proximal side of the press-side engagement portion 32 are approximately perpendicular to the center axis of the shaft portion 20.

The interlock portion 70 is a tubular body that transmits the movement force of the outer tube 30 toward the axial direction to the slide portion 50. The interlock portion 70 includes a distal side fixing portion 78, a movement-side engagement portion 71, a first receiving portion 74, a second receiving portion 75, a first tubular portion 76, and a second tubular portion 77. The movement-side engagement portion 71 is provided with a first movement-side engagement portion 72, and a second movement-side engagement portion 73. The distal side fixing portion 78 covers the slide portion 50, and is fixed to the slide portion 50.

The first movement-side engagement portion 72 is a portion that is capable of attaching to or engaging with (directly contacting) the press-side engagement portion 32. The first movement-side engagement portion 72 is positioned on the proximal side from the distal side fixing portion 78. The first movement-side engagement portion 72 protrudes inward in the radial direction. The first movement-side engagement portion 72 is positioned on the distal side of the press-side engagement portion 32. A surface on the proximal side of the first movement-side engagement portion 72 is approximately perpendicular to the axial center of the shaft portion 20. An inner diameter of the first movement-side engagement portion 72 is larger than an outer diameter of the shaft body 21, and is smaller than an outer diameter of the press-side engagement portion 32. Accordingly, a surface on the proximal side of the first movement-side engagement portion 72 is capable of attaching to or engaging with the press-side engagement portion 32 that moves to the distal side.

The second movement-side engagement portion 73 is a portion capable of attaching to or engaging with (directly contacting) the press-side engagement portion 32. The second movement-side engagement portion 73 is positioned on the proximal side from the first movement-side engagement portion 72. The second movement-side engagement portion 73 protrudes inward in the radial direction. The second movement-side engagement portion 73 is positioned on the proximal side of the press-side engagement portion 32. A surface on the distal side of the second movement-side engagement portion 73 is approximately perpendicular to the axial center of the shaft portion 20. An inner diameter of the second movement-side engagement portion 73 is larger than the outer diameter of the outer tube main body 31, and is smaller than the outer diameter of the press-side engagement portion 32. Accordingly, the surface on the distal side of the second movement-side engagement portion 73 is capable of attaching to or engaging with the press-side engagement portion 32 that moves to the proximal side.

The first receiving portion 74 is formed continuously from the first movement-side engagement portion 72 on the distal side of the first movement-side engagement portion 72. An inner peripheral surface of the first receiving portion 74 comes into close contact with the outer peripheral surface of the shaft body 21 with a prescribed clearance. The inner peripheral surface of the first receiving portion 74 is capable of smoothly sliding with respect to and along the outer peripheral surface of the shaft body 21.

The second receiving portion 75 is formed continuously from the second movement-side engagement portion 73 on the proximal side of the second movement-side engagement portion 73. An inner peripheral surface of the second receiving portion 75 comes into close contact with the outer peripheral surface of the outer tube main body 31 with a prescribed clearance. The inner peripheral surface of the second receiving portion 75 is capable of smoothly sliding with respect to and along the outer peripheral surface of the outer tube main body 31.

The first tubular portion 76 is a tubular portion that is positioned between the distal side fixing portion 78 and the first receiving portion 74. An inner diameter of the first tubular portion 76 is larger than an outer diameter of the proximal side stopper 24. Accordingly, the first tubular portion 76 provides an internal space in which the proximal side stopper 24 is movable in the axial direction.

The second tubular portion 77 is a tubular portion that is positioned between the first movement-side engagement portion 72 and the second movement-side engagement portion 73. An inner diameter of the second tubular portion 77 is larger than the outer diameter of the press-side engagement portion 32. Accordingly, the second tubular portion 77 provides an internal space in which the press-side engagement portion 32 is movable in the axial direction. A length of the second tubular portion 77 in the axial direction is longer than a length of the press-side engagement portion 32 in the axial direction. Therefore, the press-side engagement portion 32 is movable in the axial direction in the inside of the second tubular portion 77 that is positioned between the first movement-side engagement portion 72 and the second movement-side engagement portion 73.

The interlock portion 70 preferably has flexibility greater than and has flexural rigidity less than the shaft portion 20 so as not to hinder an operation of the shaft portion 20. A Examples of a material from which the interlock portion 70 may be made is not specially limited Examples of the material from which the interlock portion 70 may be made include thermoplastic polyester elastomer, polyolefin such as polyethylene or polypropylene, polyamide, polyester such as polyethylene terephthalate, a fluorinated polymer such as polytetrafluoroethylene (PTFE) or tetrafluoroethylene ethylene copolymer (ETFE), polyether ether ketone (PEEK), polyimide.

The operation unit 80 is a portion that is gripped and operated by an operator. The operation unit 80 is provided with, as illustrated in FIG. 1, a casing 81, a first gear 82 that is fixed to the shaft body 21, and an operation handle 83 that is fixed to the outer tube 30. The casing 81, through which the shaft portion 20 penetrates, houses therein a proximal end of the outer tube 30. A part of the first gear 82 is disposed in the casing 81, and another part of the first gear 82 is exposed outward from an opening portion 84 of the casing 81. A part of the operation handle 83 is disposed in the casing 81, and another part of the operation handle 83 is positioned outward of the casing 81. The operation handle 83 is movable in the axial direction relative to the casing 81. The operation handle 83 is fixed to the outer tube 30 in an inside of the casing 81. Accordingly, the operation handle 83 moves in the axial direction, whereby the outer tube 30 moves in the axial direction relative to the shaft portion 20.

The driving unit 90 is a portion that rotationally drives the shaft portion 20. The driving unit 90 is provided with a drive source 91 such as a motor, a second gear 92 that is rotated by the drive source 91, and a connector 93 that is interlocked with the operation unit 80. The connector 93 is interlocked with the operation unit 80, whereby the second gear 92 and the first gear 82 mesh with each other. Accordingly, the drive source 91 is rotated to rotate the shaft portion 20. The drive source 91 is configured to rotate in opposite directions. The drive source 91 is not limited to one that rotates in opposite directions, but may rotate in one direction.

A method of operating/using the medical device 10 according to the above-described embodiment will be explained using a case where a thrombus B in the blood vessel is broken as an example.

First, as illustrated in FIG. 3(B), the medical device 10 in a state where the distal portion of the shaft portion 20 including the expandable portion 60 is housed in the sheath 100 is prepared. Next, a guide wire 110 (see FIG. 4) is inserted into the shaft portion 20. Subsequently, the sheath 100 and the expandable portion 60 housed in the sheath 100 are moved in the blood vessel while being guided along the guide wire 110 to reach the vicinity of the thrombus B. Thereafter, when the sheath 100 is moved to the proximal side relative to the medical device 10 or is moved in the proximal direction, as illustrated in FIGS. 2 and 3(A), the expandable portion 60 is exposed outside the sheath 100. That is, the expandable portion 60 is exposed distal of the distal end of the sheath 100. Accordingly, the expandable portion 60 expands by the self-elastic force or self-expanding force, and shifts to a first expanded state. At this time, the slide portion 50 slides along the guide convex portion 22 on the outer peripheral surface of the shaft body 21 to the distal side or in the distal direction. When the expandable portion 60 shifts from a contracted state while housed in the sheath 100 to the first expanded state upon automatic outward expansion by virtue of the self-expanding force, the expandable portion 60 moves by a first distance L1 in the axial direction, and outwardly expands. In the first expanded state, a second distance L2 between the distal side stopper 23 and the slide portion 50 is longer than the first distance L1. Next, as illustrated in FIG. 1, the driving unit 90 is interlocked with the operation unit 80. Next, when the drive source 91 is operated (i.e., when the driving source 91 is turned on), the shaft portion 20 rotates, and the fixing portion 40 and the guide convex portion 22 fixed to the shaft portion 20 rotate. Accordingly, the expandable portion 60 rotates by receiving the rotation force from the fixing portion 40, and the slide portion 50 interlocked with the guide convex portion 22. Subsequently, when the expandable portion 60 is caused to reciprocate in the axial direction in the blood vessel, the expandable portion 60 comes into contact with the thrombus B, and breaks the thrombus B. The expandable portion 60 repeats the rotation and the stop of rotation. Accordingly, the expandable portion 60 repeats the operation of cutting into the thrombus B at the stop of rotation, and scraping the thrombus B off (crushing or destroying the thrombus B) by the rotation.

When the breaking force is desired to be increased, the operation handle 83 is moved to the distal side or in the distal direction. Accordingly, the outer tube 30 interlocked with the operation handle 83 moves to the distal side or in the distal direction. Accordingly, as illustrated in FIG. 4, the press-side engagement portion 32 contacts or engages the first movement-side engagement portion 72, and causes the first movement-side engagement portion 72 to move to the distal side or in the distal direction. That is, the press-side engagement portion 32 is brought into contacting engagement with the first movement-side engagement portion 72, and the first movement-side engagement portion 72 moves in the axial direction together with the outer tube 30 and the press-side engagement portion 32. Accordingly, the interlock portion 70 and the slide portion 50 move to the distal side or in the distal direction relative to the shaft portion 20. When the slide portion 50 moves to the distal side, the distance between the fixing portion 40 and the slide portion 50 becomes shorter or is reduced. Accordingly, the expandable portion 60 outwardly expands in the radial direction, thereby expanding to an outer size larger than the outer size of the expandable portion 60 in the first expanded state. Accordingly, as indicated by the black arrows in FIG. 4, a portion of the expandable portion 60 already in contact with the thrombus B in the first expanded state comes into stronger contact with the thrombus B. Moreover, as indicated by the white arrows in FIG. 4, a part of the expandable portion 60 not in contact with the thrombus B in the first expanded state outwardly expands in the radial direction and comes into contact with the thrombus B. Therefore, the breaking force of the expandable portion 60 is increased. The operator can change the breaking force of the expandable portion 60 by adjusting the movement amount of the operation handle 83. When the operation handle 83 is moved to the distal side or in the distal direction, the slide portion 50 moves closer to the distal side stopper 23. When the slide portion 50 comes into contact with the distal side stopper 23, further movement of the slide portion 50 is restricted or prevented. Accordingly, for safety, further expansion of the expandable portion 60 is restricted. The slide portion 50 can move to the distal side from the self-expanded first state, within a range of the second distance L2.

Figure 5:
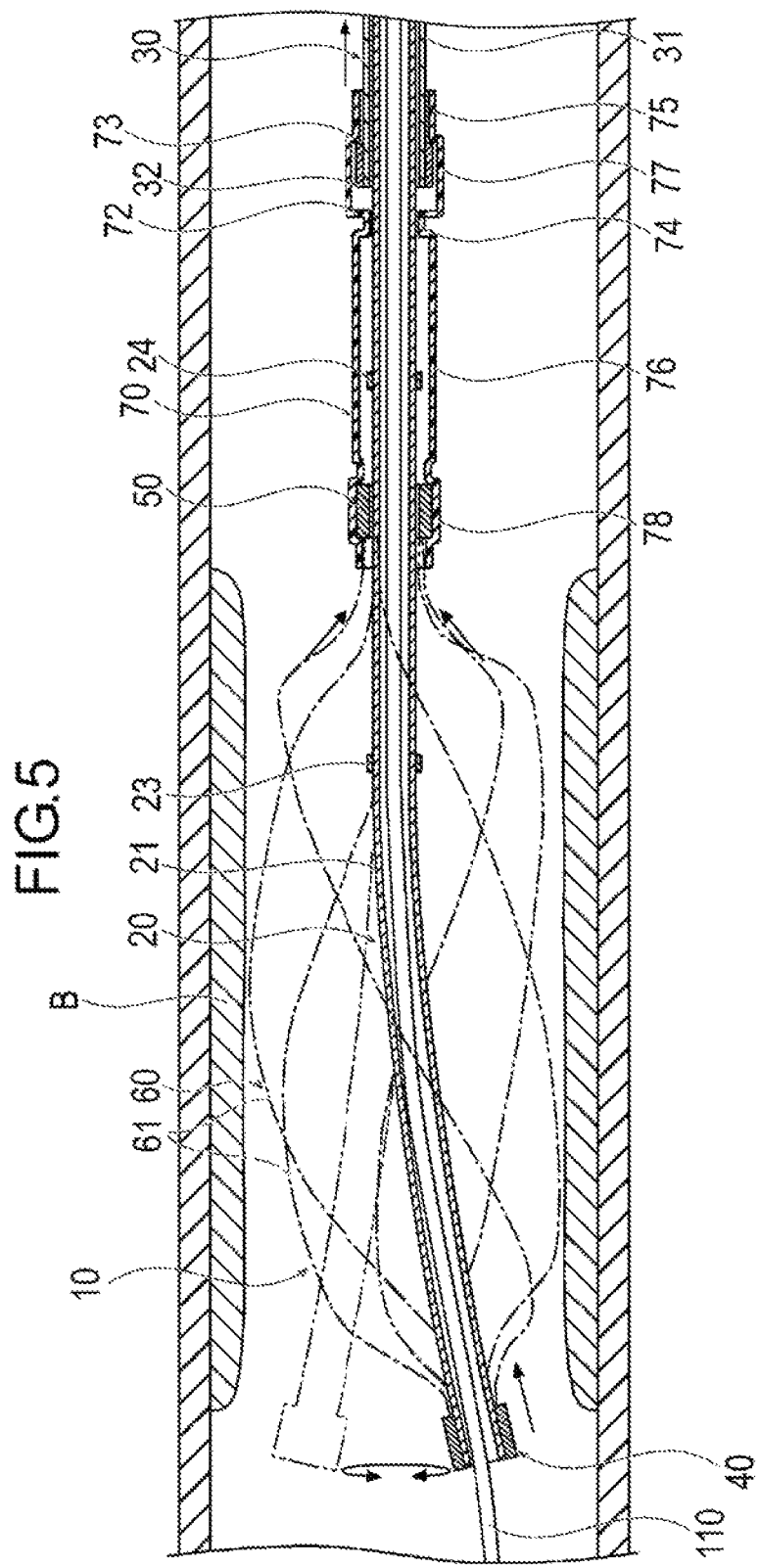
FIG. 5 is a cross-sectional view illustrating a state where a shaft portion is curved in the blood vessel.

Moreover, when the breaking force is desired to be increased, the operation handle 83 may be caused to move to the proximal side. Accordingly, the outer tube 30 interlocked with the operation handle 83 moves to the proximal side or in the proximal direction. Accordingly, as illustrated in FIG. 5, the press-side engagement portion 32 contacts or is engaged with the second movement-side engagement portion 73, and causes the second movement-side engagement portion 73 to move to the proximal side or in the proximal direction. Therefore, the interlock portion 70 and the slide portion 50 move to the proximal side relative to the shaft portion 20. When the slide portion 50 moves to the proximal side or in the proximal direction, a force toward the proximal side acts on the fixing portion 40. Accordingly, the shaft body 21 having flexibility is curved in an inner side of the expandable portion 60. When the shaft body 21 rotates in this state, the distal end of the curved shaft body 21 swings around, the expandable portion 60 rotates about the swung-around shaft body 21. Therefore, an influence range of the expandable portion 60 increases. Accordingly, the breaking force of the expandable portion 60 increases. The operator can change the breaking force of the expandable portion 60 by adjusting the movement amount of the operation handle 83.

After the thrombus B has been broken by the expandable portion 60, the drive source 91 is stopped to stop the rotation of the shaft portion 20. Next, the expandable portion 60 and the sheath are relatively axially moved so that the expandable portion 60 is housed in the sheath 100. Next, the medical device 10 is extracted from the blood vessel, and the procedure using the medical device 10 is completed. The broken thrombus B is sucked (e.g., aspirated) and removed by, for example, the sheath 100 or another device.

The medical device 10 according to the present embodiment is a medical device 10 for destroying (e.g., crushing or cutting) the thrombus B (object) in the blood vessel (body lumen in a living body), and includes: the elongated shaft portion 20 that is rotationally driven; the expandable portion 60 that is provided to the distal portion of the shaft portion 20; the fixing portion 40 to which the distal end of the expandable portion 60 and the shaft portion 20 are fixed; the slide portion 50 that is fixed to the proximal end of the expandable portion 60, and is interlocked with the shaft portion 20 slidably in the axial direction; and the outer tube 30 that houses therein the shaft portion 20, and is movable in the axial direction along the shaft portion 20, in which the slide portion 50 is movable by being indirectly pressed by the outer tube 30, and the slide portion 50 is relatively rotatable relative to the outer tube 30. The outer tube 30 may be movable in the axial direction along the shaft portion 20, and also rotatable.

In the medical device 10 configured in the manner described above, the slide portion 50 can move to the distal side or the proximal side by moving the outer tube 30 in the axial direction. The slide portion 50 moves to the distal side or the proximal side to deform the expandable portion 60 that is positioned between the fixing portion 40 and the slide portion 50. Therefore, in the medical device 10, during when the rotating expandable portion 60 breaks the thrombus B (object), it is possible to adjust the breaking force of the expandable portion 60. In addition, the slide portion 50 relatively rotates with respect to the outer tube 30. Therefore, the rotation force is not so likely to be transmitted from the rotating slide portion 50 to the outer tube 30, which results in an easy operation by the operator.

Moreover, the medical device 10 includes the interlock portion 70 that is fixed to and movable with the slide portion 50 and is movable in the axial direction along the shaft portion 20, the outer tube 30 includes the press-side engagement portion 32 that protrudes in the radial direction, the interlock portion 70 includes the movement-side engagement portion 71 that protrudes in the radial direction on at least one of the distal side and proximal side of the press-side engagement portion 32, and the interlock portion 70 is moved because the press-side engagement portion 32 is engaged or in contact with the movement-side engagement portion 71 by the outer tube 30, and causes the slide portion 50 to move. Accordingly, in the medical device 10, it is possible to indirectly press the slide portion 50 via the interlock portion 70 by the outer tube 30. Therefore, by disposing the interlock portion 70 having a structure desired to cause the slide portion 50 to move, it is possible to effectively cause the slide portion 50 to move. The interlock portion 70 may be movable in the axial direction along the shaft portion 20, and also rotatable. Moreover, the interlock portion 70 is fixed to the slide portion 50, but does not need to be completely fixed to the slide portion. For example, the interlock portion 70 and the slide portion 50 may be fixed to each other to the extent that the interlock portion 70 and the slide portion 50 mutually constrain the movement and can integrally move together as a unit.

Also, the interlock portion 70 is connected to the slide portion 50 and is independent of the outer tube 30, and thus is relatively rotatable relative to the outer tube 30. Accordingly, the outer tube 30 is not connected to but is independent of the rotating interlock portion 70 and the rotating expandable portion, and thus suppresses the rotation of the handle that is connected to the proximal portion of the outer tube 30. Therefore, the usability of the medical device 10 is improved.

Moreover, the slide portion 50 is disposed to be in contact with the guide convex portion 22 that restricts the rotation of the slide portion 50, and transmits the rotation force to the slide portion 50. Accordingly, the slide portion 50 receives the rotation force from the guide convex portion 22, and rotates together with the guide convex portion 22. Therefore, the slide portion 50 can receive a torsion force that is generated due to friction or the like between the outer tube 30 and the interlock portion 70. Therefore, it is possible to suppress the expandable portion 60 to which the slide portion 50 is fixed from twisting, and maintain the expandable portion 60 in a suitable state.

Additionally, the movement-side engagement portion 71 includes the first movement-side engagement portion 72 that protrudes in the radial direction on the distal side of the press-side engagement portion 32, and the outer tube 30 moves to the distal side relative to the shaft portion 20 to cause the press-side engagement portion 32 to be engaged with the first movement-side engagement portion 72. Accordingly, by causing the outer tube 30 to move to the distal side or in the distal direction, it is possible to press the first movement-side engagement portion 72 by the press-side engagement portion 32, and to cause the interlock portion 70 and the slide portion 50 to move to the distal side or in the distal direction. The slide portion 50 moves to the distal side, so that the expandable portion 60 that is positioned between the fixing portion 40 and the slide portion 50 expands outward in the radial direction. Therefore, the medical device 10 can adjust the diameter of the rotating expandable portion 60 as desired for destroying the object in a rotation state.

Moreover, the movement-side engagement portion 71 includes the second movement-side engagement portion 73 that protrudes in the radial direction on the proximal side of the press-side engagement portion 32, and the outer tube 30 moves to the proximal side relative to the shaft portion 20 to cause the press-side engagement portion 32 to be engaged with the second movement-side engagement portion 73. Accordingly, by causing the outer tube 30 to move to the proximal side or in the proximal direction, it is possible to press the second movement-side engagement portion 73 by the press-side engagement portion 32, and to cause the interlock portion 70 and the slide portion 50 to move to the proximal side or in the proximal direction. The slide portion 50 moves to the proximal side to apply a force toward the proximal side on the distal portion of the shaft portion 20 via the fixing portion 40. Accordingly, it is possible to bend the shaft portion 20. When the bent shaft portion 20 is rotated, the distal portion of the shaft portion 20 swings around, meaning the path of movement of the bent shaft portion 20 is larger than if the shaft portion 20 rotated while not bent. Accordingly, the expandable portion 60 that is rotationally driven by the swinging-around shaft portion 20 can expand a range in which a breaking effect acts.

Moreover, the expandable portion 60 becomes a first expanded state in a natural state where no external force acts, and outwardly expands in the radial direction more than in the first expanded state by the movement-side engagement portion 71 moving to the distal side relative to the shaft portion 20. Accordingly, the object can be broken by the expandable portion 60 in the first expanded state, and can be effectively broken by the expandable portion 60 having a larger diameter resulting from the further outward expansion.

Moreover, the press-side engagement portion 32 is capable of separating from the first movement-side engagement portion 72. Accordingly, only in a case where the expandable portion 60 is caused to outwardly expand, it is possible to make the press-side engagement portion 32 closer to the first movement-side engagement portion 72, to press the first movement-side engagement portion 72 by the press-side engagement portion 32. Therefore, it is possible to suppress the expandable portion 60 from unintentionally expanding, so that safety is improved. Moreover, the press-side engagement portion 32 is capable of separating from the second movement-side engagement portion 73. Accordingly, only in a case where a range to be covered by the breaking effect of the expandable portion 60 is desired to be increased, it is possible to make the press-side engagement portion 32 closer to the second movement-side engagement portion 73, and press the second movement-side engagement portion 73 by the press-side engagement portion 32. Therefore, it is possible to suppress the range to be covered by the breaking effect of the expandable portion 60 from unintentionally expanding, so that the safety is improved.

Moreover, surfaces of the press-side engagement portion 32 and the first movement-side engagement portion 72 to be engaged with each other or in contact with each other are perpendicular to the axial center (center axis) of the shaft portion 20. Therefore, it is possible to press the first movement-side engagement portion 72 that rotates by the press-side engagement portion 32 that does not rotate, without hindering the rotation. Moreover, surfaces of the press-side engagement portion 32 and the second movement-side engagement portion 73 to be engaged with each other are perpendicular to the axial center of the shaft portion 20. Therefore, it is possible to press second movement-side engagement portion 73 that rotates by the press-side engagement portion 32 that does not rotate, without hindering the rotation.

Moreover, the interlock portion 70 includes the first receiving portion 74 formed with an inner peripheral surface that slides with an outer peripheral surface of the shaft portion 20, and the second receiving portion 75 formed with an inner peripheral surface that slides with an outer peripheral surface of the outer tube 30. Accordingly, the interlock portion 70 is disposed accurately and coaxially with the shaft portion 20 and the outer tube 30. Accordingly, the first movement-side engagement portion 72 and the second movement-side engagement portion 73 are engaged with the press-side engagement portion 32 at suitable positions. Accordingly, it is possible to smoothly and effectively move the first movement-side engagement portion 72 and/or the second movement-side engagement portion 73, by the press-side engagement portion 32.

Moreover, the medical device 10 according to the present embodiment is the medical device 10 for destroying the thrombus B (object) in a blood vessel (body lumen), and includes: the elongated shaft portion 20 that is rotationally driven; the expandable portion 60, including the wire rods 61 having shape memory characteristics, that is provided to the distal portion of the shaft portion 20, and outwardly expands by a self-elastic or self-expansion force from a contracted state by moving in the axial direction by the first distance L1; the fixing portion 40 that fixes the distal end of the expandable portion 60 and the shaft portion 20; the slide portion 50 that is fixed to the proximal end of the expandable portion 60, and is interlocked with the shaft portion 20 slidably in the axial direction; the distal side stopper 23 and the proximal side stopper 24 that are provided to the shaft portion 20, and restrict the movement of the slide portion 50; and the outer tube 30 that is movable in the axial direction along the shaft portion 20, and causes the slide portion 50 to move, in which a distance between the distal side stopper 23 and the proximal side stopper 24 is longer than the first distance L1, and an expanded diameter of the expandable portion 60 becomes, by causing the outer tube 30 to move such that the second distance L2 between the slide portion 50 and the distal side stopper 23 in a state where the expandable portion 60 has expanded by the self-elastic force, larger than the expanded diameter in the expanded state by the self-elastic force.

The medical device 10 configured as the above can restrict the expansion of the expandable portion 60 by restricting the movement of the slide portion 50 by the distal side stopper 23. Therefore, it is possible to suppress the expandable portion 60 from expanding beyond the assumption, and reduce a burden of a target body lumen. Meanwhile, for example, there is a case where the expandable portion 60 cannot expand to an assumed expanded diameter by only the self-elastic or self-expanding force because an object such as a thrombus in the target body lumen is hard. In this case, the operator can enlarge the expanded diameter of the expandable portion 60 by manually operating the medical device 10. In other words, the operator causes the outer tube 30 to move to cause the slide portion 50 to move, and thus can obtain the expanded diameter larger than the assumed expanded diameter in the natural state. Accordingly, the operator can arbitrarily increase the breaking force of the expandable portion 60. Note that, even in a case where the operation is made so as to make the expanded diameter of the expandable portion 60 large, when the expandable portion 60 is in contact with an object to be broken in the body lumen, there is a possibility that the expanded diameter in appearance does not become large. However, even in such a case, the expandable portion 60 has an expanded diameter in a state where no force is received from an object to be cut larger than the assumed expanded diameter in the natural state.

Moreover, the first distance L1 is longer than the second distance L2. Accordingly, the degree of expansion of the expandable portion 60 that self-expands by the first distance L1 is larger than the degree of expansion of the expandable portion 60 that further expands by the second distance L2. Therefore, the expandable portion 60 that has self-expanded by the first distance L1 can be mainly used. Further, the expandable portion 60 that has further expanded within the range of the second distance L2 to improve the breaking force can be used for additional breaking. At this time, the second distance L2 for additionally increasing the breaking force is shorter than the first distance L1 for causing the expandable portion 60 to self-expand, so that the safety of the medical device 10 is improved.

Moreover, the medical device 10 further includes the interlock portion 70 that rotatably houses therein the shaft portion 20, and is movable in the axial direction along the shaft portion 20, in which the outer tube 30 includes the press-side engagement portion 32 that protrudes in the radial direction, the interlock portion 70 includes the movement-side engagement portion 71 that protrudes in the radial direction on at least one of the distal side or the proximal side of the press-side engagement portion 32, and the outer tube 30 moves to engage the press-side engagement portion 32 with the movement-side engagement portion 71 to cause the interlock portion 70 to move, so that the slide portion 50 moves.

In the medical device 10 configured as the above, the outer tube 30 is caused to move in the axial direction to cause the press-side engagement portion 32 to press the movement-side engagement portion 71, so that it is possible to cause the interlock portion 70 and the slide portion 50 to move to the distal side or the proximal side. The slide portion 50 moves to the distal side or the proximal side to deform the expandable portion 60 that is positioned between the fixing portion 40 and the slide portion 50. Therefore, in the medical device, during when the rotating expandable portion 60 breaks the object, it is possible to adjust the breaking force of the expandable portion 60.

This disclosure is not limited to the above-described embodiment, as various changes by those skilled in the art can be made within the technical scope of this disclosure. For example, the body lumen into which the medical device 10 is inserted is not limited to the blood vessel, but may be the vessel, the ureter, the bilary duct, the oviduct, or the hepatic duct, for example. Accordingly, an object to be destroyed (e.g., crushed or cut) does not need to be the thrombus B.

Moreover, in the abovementioned embodiment, because the shaft body 21 is flexible, by moving the operation handle 83 to the proximal side, the shaft body 21 is bent, so that it is possible to increase the range covered by the breaking force (see FIG. 5). However, it is also possible to make the shaft body 21 difficult to bend, by setting the flexural rigidity of the shaft body 21 that is positioned in the inner side of the expandable portion 60 harder. In this case, by causing the operation handle 83 to move to the proximal side, the slide portion 50 is separated from the fixing portion 40, and the diameter of the expandable portion 60 is reduced. Therefore, it is possible to decrease the breaking force of the expandable portion 60 by adjusting the movement amount of the operation handle 83. Accordingly, the medical device 10 may only include the second movement-side engagement portion 73, without including the first movement-side engagement portion 72.

Moreover, the wire rods 61 included in the expandable portion 60 do not need to be spiral-shaped, but may be linear in the axial direction in a circumferential development view, for example.

Moreover, either one of the press-side engagement portion 32 and the first movement-side engagement portion 72 that are engaged with each other does not need to be provided on the entire circumference at over 360 degrees. The press-side engagement portion 32 and the first movement-side engagement portion 72 can be engaged with each other while allowing the relative rotation, even when one of the press-side engagement portion 32 and the first movement-side engagement portion 72 is partially provided in the circumferential direction. Similarly, either one of the press-side engagement portion 32 and the second movement-side engagement portion 73 that are engaged with each other does not need to be provided on the entire circumference at over 360 degrees. Moreover, although in the present embodiment, the press-side engagement portion 32 protrudes outward in the radial direction, and the first movement-side engagement portion 72 and the second movement-side engagement portion 73 protrude inward in the radial direction, the reverse configuration may be employed.

Figure 6:
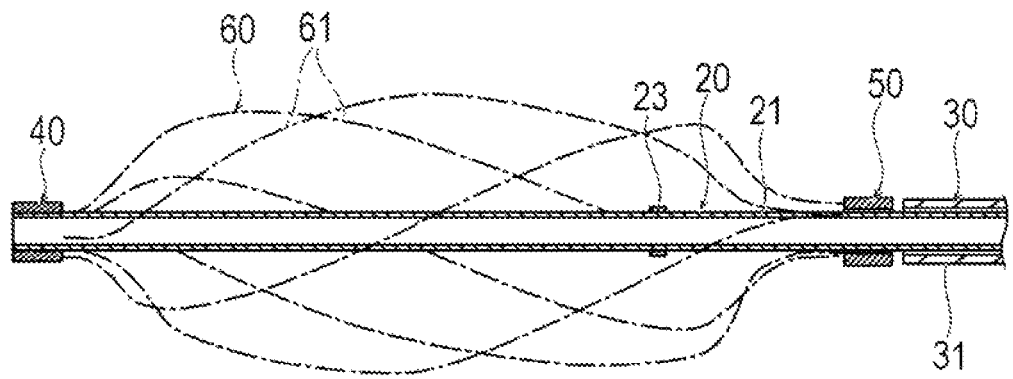
FIG. 6 is a cross-sectional view illustrating a modification example of the medical device.

Moreover, as in a modification example illustrated in FIG. 6, the medical device does not need to include an interlock portion that is fixed to the slide portion 50. In this case, the outer tube 30 moves to the distal side, so that the outer tube 30 directly presses the slide portion 50 to move the slide portion 50. The slide portion 50 is relatively rotatable with the outer tube 30 while receiving a force from the outer tube 30.

The detailed description above describes embodiments of a medical device and operational method representing examples of the inventive medical device and operational method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for destroying an object in a body lumen, the medical device comprising:
an axially movable outer tube possessing an interior;
an elongated shaft that is configured to be rotationally driven, at least a part of the elongated shaft being positioned in the interior of the outer tube, the outer tube and the elongated shaft being relatively axially movable, the elongated shaft possessing a distal end;

an expandable portion positioned at a distal portion of the elongated shaft, the expandable portion being outwardly expandable from a contracted state to an expanded state, the expandable portion possessing a distal end and a proximal end;

a fixing portion that fixes the distal end of the expandable portion to the distal end of the shaft portion so that axial movement of the elongated shaft in the axial direction results in axial movement of the expandable portion in the axial direction and so that rotation of the elongated shaft results in rotation of the expandable portion;

a slide portion that is slidably mounted on the elongated shaft to slide in the axial direction along the elongated shaft, the slide portion being fixed to the proximal end of the expandable portion so that sliding movement of the slide portion along the elongated shaft results in sliding movement of the proximal end of the expandable portion along the elongated shaft;

the slide portion is movable by being directly or indirectly pressed by the outer tube;

the slide portion and the outer tube being relatively rotatable with respect to one another;

an interlock portion that is fixed to the slide portion so that axial movement of the interlock portion results in axial movement of the slide portion, the interlock portion being movable in the axial direction relative to and along the shaft portion;

the outer tube including a press-side engagement portion that protrudes in a radial direction and moves together with the outer tube;

the interlock portion including a movement-side engagement portion that protrudes in the radial direction on a distal side or a proximal side of the press-side engagement portion, the movement-side engagement portion and the press-side engagement portion being movable into a contacting engagement with one another and out of contacting engagement with one another when the interlock portion is moved in the axial direction relative to the shaft portion; and axial movement of the outer tube in the axial direction causing the press-side engagement portion to axially move in the axial direction and move into contacting engagement with the movement-side engagement portion, the contacting engagement between the press-side engagement portion and the movement-side engagement portion during the axial movement of the outer tube in the axial direction causing the interlock portion and the slide portion to axially move in the axial direction relative to the elongated shaft.

2. The medical device according to claim 1, wherein the movement-side engagement portion includes a first movement-side engagement portion that protrudes in the radial direction on the distal side of the press-side engagement portion, and the axial movement of the outer tube toward the distal side relative to the shaft portion causes the press-side engagement portion to move into contacting engagement with the first movement-side engagement portion.

3. The medical device according to claim 1, wherein the movement-side engagement portion includes a second movement-side engagement portion that protrudes in the radial direction on the proximal side of the press-side engagement portion, and the axial movement of the outer tube toward the proximal side relative to the shaft portion causes the press-side engagement portion to move into contacting engagement with the second movement-side engagement portion.

4. The medical device according to claim 1, wherein the expanded state is a first expanded state of the expandable portion, the first expanded state being a natural state of the expandable portion in which no force is applied to the expandable portion, and the expandable portion expanding outwardly in the radial direction more than in the first expanded state by the movement-side engagement portion moving to the distal side relative to the shaft portion.

5. The medical device according to claim 1, wherein the press-side engagement portion is separable from the movement-side engagement portion so that the press-side engagement portion moves out of contacting engagement with the movement-side engagement portion.

6. The medical device according to claim 1, wherein the elongated shaft includes a center axis, the press-side engagement portion and the movement-side engagement portion each including axially opposite end surfaces that are perpendicular to the center axis of the shaft portion.

7. The medical device according to claim 1, wherein the interlock portion includes a first receiving portion possessing an inner peripheral surface that slides along an outer peripheral surface of the elongated shaft, and a second receiving portion spaced proximally from the first receiving portion and possessing an inner peripheral surface that slides along an outer peripheral surface of the outer tube.

8. The medical device according to claim 1, wherein the slide portion is in contact with a guide portion that is fixed to the elongated shaft, the guide portion preventing rotation of the slide portion relative to the elongated shaft and transmitting a rotation force applied by rotation of the elongated shaft to the slide portion.

9. A medical device for destroying an object in a body lumen, the medical device comprising:

an axially movable outer tube possessing an interior;

an elongated shaft that is configured to be rotationally driven, at least a part of the elongated shaft being positioned in the interior of the outer tube, the outer tube and the elongated shaft being relatively axially movable in an axial direction, the elongated shaft possessing a distal end;

an expandable portion comprised of a plurality of wires each having shape memory characteristics, each of the wires possessing a distal end and a proximal end, the expandable portion possessing an intermediate portion, the plurality of wires at least in the intermediate part of the expandable portion being spaced apart from one another, the expandable portion being outwardly expandable from a contracted state to an expanded state by virtue of a self-elastic force of each of the plurality of wires, the expandable portion moving a first distance in the axial direction as the expandable portion moves from the contracted state to the expanded state, the expandable portion in the expanded state possessing a first outer diameter;

a fixing portion that fixes the distal end of each of the plurality of wires to the distal end of the elongated shaft;

a slide portion that is slidably mounted on the elongated shaft to slide in the axial direction along the elongated shaft, the slide portion being axially slidable in the axial direction relative to the elongated shaft, the slide portion being fixed to the proximal end of each of the plurality of wires so that sliding movement of the slide portion along the elongated shaft results in sliding movement of the proximal end of each of the plurality of wires along the elongated shaft;

a distal side stopper and a proximal side stopper fixed to the elongated shaft to restrict movement of the slide portion;

an axial distance between the distal side stopper and the proximal side stopper is greater than the first distance;

the expandable portion expanding outwardly from the first outer diameter to a second outer diameter that is larger than the first outer diameter when the outer tube is moved in the axial direction by a second distance so that the slide portion moves toward the distal side stopper.

10. The medical device according to claim 9, wherein the first distance is greater than the second distance.

11. The medical device according to claim 9, further comprising an interlock portion through which passes the elongated shaft, and the interlock portion being movable in the axial direction along the shaft portion;

the outer tube including a press-side engagement portion that protrudes in a radial direction;

the interlock portion including a movement-side engagement portion that protrudes in the radial direction on a distal side or a proximal side of the press-side engagement portion, the movement-side engagement portion and the press-side engagement portion being movable into a contacting engagement with one another and out of contacting engagement with one another when the interlock portion is moved in the axial direction relative to the shaft portion; and axial movement of the outer tube in the axial direction causing the press-side engagement portion to axially move in the axial direction and move into contacting engagement with the movement-side engagement portion, the contacting engagement between the press-side engagement portion and the movement-side engagement portion during the axial movement of the outer tube in the axial direction causing the interlock portion and the slide portion to axially move in the axial direction relative to the elongated shaft.

12. The medical device according to claim 9, wherein the interlock portion is connected to the slide portion so that the interlock portion and the slide portion move together, the interlock portion being independent of the outer tube and relatively rotatable relative to the outer tube.

13. The medical device according to claim 9, wherein the axial distance between the proximal side stopper and the slide portion increases as the expandable portion moves from the contracted state to the expanded state, and the axial distance between the distal side stopper and the slide portion decreases as the expandable portion moves from the contracted state to the expanded state.

14. The medical device according to claim 9, wherein the expanded state of the expandable portion is a natural state of the expandable portion in which no force is applied to the expandable portion, the axial distance between the distal side stopper and the slide portion when the expandable portion is in the expanded state being greater than the first distance.

15. A method comprising:

positioning an expandable portion in a living body lumen in a living body while the expandable portion is in a contracted state, the expandable portion being positioned at a distal portion of an elongated shaft, an interlock portion being movable in an axial direction relative to and along the shaft, the interlock portion being fixed to a slide piece so that axial movement of the interlock portion results in axial movement of the slide piece, an axially movable outer tube possessing an interior and including a press-side engagement portion that protrudes in a radial direction and moves together with the outer tube, the interlock portion including a movement-side engagement portion that protrudes in a radial direction on a distal side or a proximal side of the press-side engagement portion, the movement-side engagement portion and the press-side engagement portion being movable into a contacting engagement with one another and out of contacting engagement with one another when the interlock portion is moved in the axial direction relative to the shaft, axial movement of the outer tube in the axial direction causing the press-side engagement portion to axially move in the axial direction and move into contacting engagement with the movement-side engagement portion, the contacting engagement between the press-side engagement portion and the movement-side engagement portion during the axial movement of the outer tube in the axial direction causing the interlock portion and the slide piece to axially move in the axial direction relative to the elongated shaft;

moving the expandable portion in the living body lumen to position the expandable portion adjacent an object in the living body lumen that is to be cut;

expanding the expandable portion from the contracted state to a first expanded state to increase an outer size of the expandable portion;

rotating the expandable portion while the expandable portion is in the first expanded state to cause the rotating expandable portion in the first expanded state to cut the object;

further expanding the expandable portion from the first expanded state to a second expanded state in which the outer size of the expandable portion in the second expanded state is greater than the outer size of the expandable portion in the first expanded state, the further expanding of the expandable portion from the first expanded state to the second expanded state occurring while the expandable portion is rotating; and rotating the expandable portion while the expandable portion is in the second expanded state to cause the rotating expandable portion in the second expanded state to further cut the object.

16. The method according to claim 15, wherein the positioning of the expandable portion in the living body lumen includes positioning the expandable portion in the living body lumen while the expandable portion is in the contracted state inside a sheath having an open distal end so that a distal end of the expandable portion is proximal of the open distal end of the sheath.

17. The method according to claim 16, wherein the expanding of the expandable portion from the contracted state to the first expanded state comprises relatively moving the expandable portion and the sheath so that the expandable portion passes through the open distal end of the sheath and is positioned completely outside the sheath, the expandable portion expanding to the first expanded state by virtue of a self-expanding force of the expandable portion, the first expanded state of the expandable portion being a natural state of the expandable portion in which no force is applied to the expandable portion.

18. The method according to claim 15, wherein the expandable portion includes a proximal portion connected to the slide piece, the slide piece being that is slidably mounted on the elongated shaft, the slide piece being connected to the outer tube by way of a linking portion so that axial movement of the outer tube results in sliding movement of the slide piece on the elongated shaft, the further expanding of the expandable portion from the first expanded state to the second expanded state comprising axially moving the outer tube in a distal direction to cause the slide piece to axially move in the distal direction by way of the linking portion.

19. The method according to claim 18, further comprising causing the elongated shaft to bend to produce a bent elongated shaft by axially moving the outer tube in a proximal direction to cause the slide piece to axially move in the proximal direction by way of the linking portion, the method further comprising rotating the expandable portion while the shaft is bent and cutting the object during the rotating of the expandable portion while the shaft is bent.

* * * * *